United States Patent
Bertola et al.

(12)

(10) Patent No.: US 6,433,193 B1
(45) Date of Patent: Aug. 13, 2002

(54) PROCESS TO AFFORD GAMMA BUTYROLACTONE AND TETRAHYDROFURAN

(75) Inventors: Aldo Bertola, Milan (IT); Take Constantinescu, Heidelberg (DE); Philippe Raucq, Lustin (BE); Salvatore Cassarino, Rome (IT)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/831,403

(22) PCT Filed: Nov. 8, 1999

(86) PCT No.: PCT/EP99/08536

§ 371 (c)(1),
(2), (4) Date: Aug. 1, 2001

(87) PCT Pub. No.: WO00/27834

PCT Pub. Date: May 18, 2000

(30) Foreign Application Priority Data

Nov. 10, 1998 (BE) .............................. 9800820

(51) Int. Cl.⁷ ...................... C07D 307/58; C07D 307/08
(52) U.S. Cl. ...................... 549/295; 549/325; 549/429; 549/508
(58) Field of Search ............... 549/429, 508, 549/325, 295

(56) References Cited

U.S. PATENT DOCUMENTS 4,609,636 A 9/1986 Mabry et al. ............... 502/183
5,149,836 A 9/1992 De Thomas et al. ........ 549/325
5,478,952 A 12/1995 Schwartz .................... 549/325

FOREIGN PATENT DOCUMENTS

| EP | 0 417 867 | 3/1991 |
| GB | 2 207 914 | 2/1989 |
| WO | WO 97/43234 | 11/1997 |
| WO | WO 97/43242 | 11/1997 |

*Primary Examiner*—Bernard Dentz
(74) *Attorney, Agent, or Firm*—Young & Thompson

(57) ABSTRACT

A process for production of tetrahydrofuran and gamma butyrolactone by hydrogenation of maleic anhydride recovered from a process of conversion of a n-butane. The process consists essentially of the following steps: A) converting n-butane to maleic anhydride by catalytic vapor phase oxidation; B) recovering maleic anhydride from the effluent gases of butane oxidation by selective absorption in gamma butyrolactone, forming a maleic anhydride-gamma butyrolactone mixture; C) removing water from the maleic anhydride-gamma butyrolactone mixture in a stripper under the action of a gas and/or under vacuum conditions, producing a maleic anhydride-gamma butyrolactone mixture with minimum water and maleic acid content; D) recovering gamma butyrolactone contained in the exhaust gases leaving the maleic anhydride absorber, by absorption in water; E) dehydrating the recovered gamma butyrolactone and recycling it to the maleic anhydride absorber; F) hydrogenating the dewatered maleic anhydride-gamma butyrolactone mixture, over suitable catalyst (s), under conditions favouring the formation of tetrahydrofuran and gamma butyrolactone; G) separating by distillation tetrahydrofuran, gamma butyrolactone and the by-products from the resulting hydrogenation mixture; H) recycling a gamma butyrolactone rich stream to the selective absorption of maleic anhydride.

31 Claims, 1 Drawing Sheet

PROCESS TO AFFORD GAMMA BUTYROLACTONE AND TETRAHYDROFURAN

Figure 1:
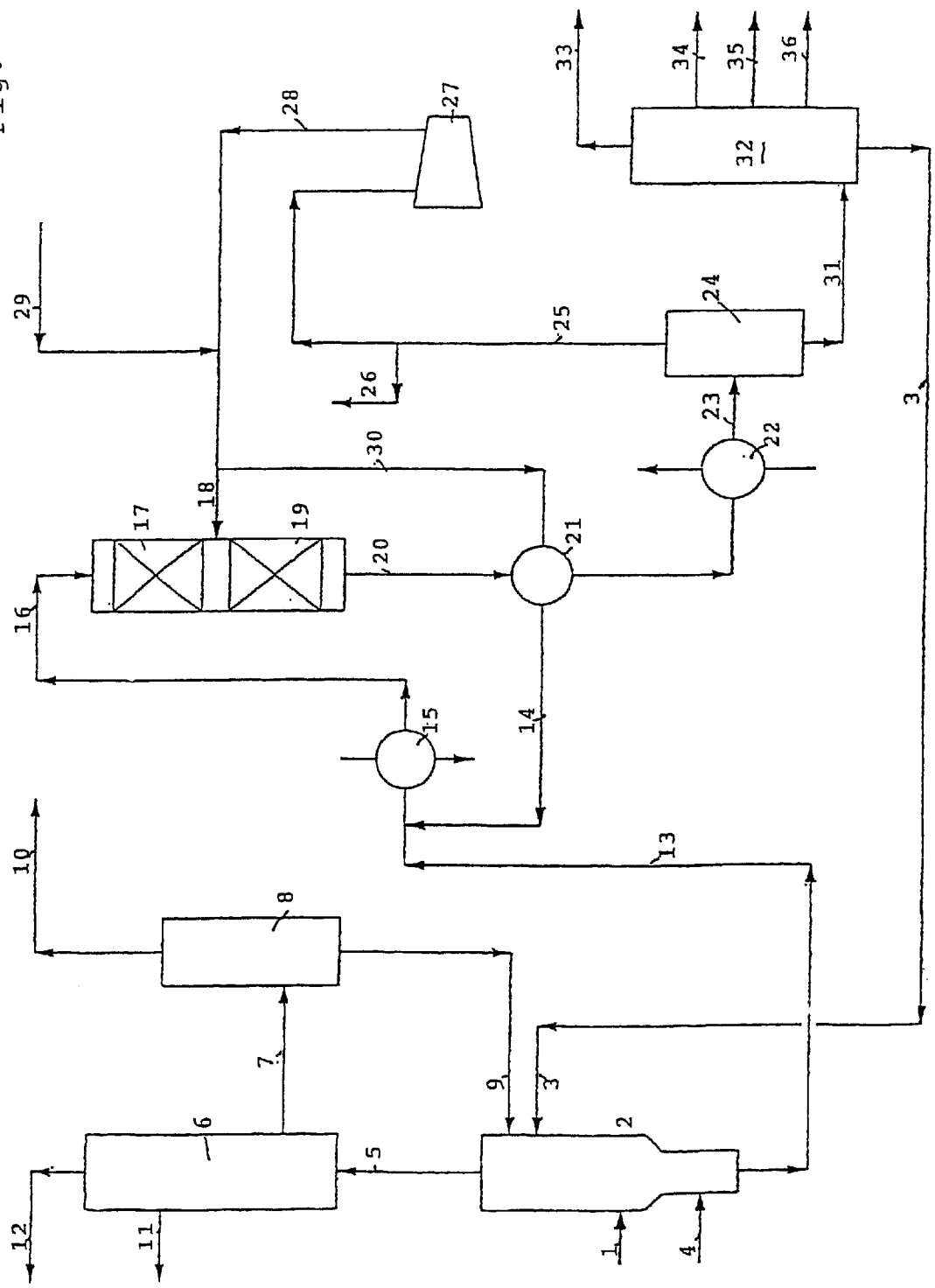

This application is a 371 of PCT/EP99/08536 filed Nov. 8, 1999.

The present invention relates to the production of tetrahydrofuran and gamma butyrolactone by hydrogenation of crude or refined maleic anhydride recovered from the off gases from the catalytic vapour phase oxidation of n-butane.

Due to the reduced production costs from n-butane, maleic anhydride (MAN) is a very attractive starting material for the production of derivatives like tetrahydrofuran (THF), gamma butyrolactone (GBL) and butanediol (BDO) by catalytic hydrogenation.

Several procedures have been disclosed for making GBL, THF and BDO via hydrogenation of MAN and/or carboxylic acids, expecially maleic acid. The following patents can be cited:

| U.S. Pat. No. | U.S. Pat. No. | U.S. Pat. No. |
|---|---|---|
| 5,502,217 | 5,473,086 | 4,985,572 |
| U.S. Pat. No. | U.S. Pat. No. | U.S. Pat. No. |
| 4,973,717 | 4,973,713 | 4,827,001 |
| U.S. Pat. No. | U.S. Pat. No. | U.S. Pat. No. |
| 4,810,807 | 4,782,167 | 4,772,729 |
| U.S. Pat. No. | U.S. Pat. No. | U.S. Pat. No. |
| 4,659,686 | 4,609,636 | 4,550,185 |
| U.S. Pat. No. | U.S. Pat. No. | U.S. Pat. No. |
| 4,550,150 | 4,155,919 | 4,096,156 |
| U.S. Pat. No. | U.S. Pat. No. | |
| 3,957,827 | 3,370,067 | |
| JP 32,439/74 | JP 43,683/69 | |
| DE 2,715,667 | DE 2,605,107 | DE 2,553,761 |
| DE 2,519,817 | | |
| GB 1,551,741 | GB 1,534,232 | |
| FR 2,505,819 | FR 2,310,331 | |
| EP 0 745 589 A1 | EP 0 722 923 A3 | EP 0 543 340 A1 |
| EP 0 417 867 A1 | EP 0 285 420 A1 | EP 0 277 562 B1 |
| EP 0 198 682 A2 | EP 0 198 681 A2 | EP 0 147 219 B1 |
| PCT 92/02,298 | | |

Several different catalysts have been proposed for the conversion of MAN into GBL,THF and/or BDO. As taught by these patents, a performant catalytic system comprises an element of the VII B group of the Mendeleev Periodic Table, preferably Rhenium or a compound thereof, associated with at least one noble metal of group VIII, preferably Palladium or a compound thereof, on a carbon or inert oxide support.

A catalyst of this kind has been first described by GB Pat. 1,551,741 and by DE Pat. 2,519,817.

As described in the technical and patent literature, MAN is fed to the hydrogenation preferably dissolved in a solvent.

U.S. Pat. No. 4,810,807 describes a hydrogenation process wherein MAN is dissolved in n-butanol.

DE Pat. No. 2,519,817 describes a process where MAN is dissolved in dioxane.

U.S. Pat. No. 4,782,167 describes a process wherein once dissolved in water, MAN is fed to hydrogenation as a maleic acid solution.

The use of organic solvents for dissolving MAN involves complex distillation steps in order to allow recovery, purification and recycling of the solvent.

On the other hand, the use of a maleic acid solution presents the advantage of simplifying the sequence of operations in the plant where butane is used as feedstock for the production of MAN.

The integration of the maleic anhydride process with the hydrogenation process results in a simplified maleic acid recovery (as opposed to MAN) and avoids MAN purification and refining.

Feeding maleic acid has, however, a negative impact on process economics since 10 to 15 mols of water are fed to the hydrogenation reactor, for each mol of MAN.

Compared with anhydrous MAN hydrogenation, where only about one mol of water forms for each mol of MAN converted to GBL or BDO, plus one additional mol per mol of THF formed, processing the reactor effluent in the presence of a large excess of water complicates THF recovery, GBL and/or BDO purification, and water separation.

Furthermore, maleic acid hydrogenation at relatively high temperature and pressure results in a corrosive environment requiring expensive construction material.

DESCRIPTION OF THE INVENTION

Therefore, the most important aim of the present invention is that of providing an optimized process for the production of GBL and THF, based on an efficient integration between the maleic anhydride process and the hydrogenation process, wherein the problems and troubles of using an aqueous maleic acid solution are solved to a great extent in an industrially convenient manner.

According to the present invention, the above aim has been accomplished by proposing a process for the production of MAN by n-butane oxidation in the vapour phase, wherein the oxidizing medium is air or, preferably, pure oxygen (or enriched air) mixed with reaction gases, and wherein MAN is recovered from the reaction gases by using an organic solvent as absorption medium, that is a solvent which is a MAN hydrogenation product at the same time, namely GBL.

The use as a solvent of a product from the process object of the present invention avoids all the drawbacks and costs associated with the recovery and purification of an additional chemical solvent which is extraneous to the process, and further avoids the high costs arising from the use of water as solvent which is described by other patents.

A further important feature of the process object of the present invention is that MAN, and not maleic acid, is essentially the major absorption product, despite the large amount of excess water which is present in the butane oxidation effluent.

Such a thing avoids the difficulties related to corrosion and also avoids the need of any expensive construction material, as it is the case when maleic acid is subjected to hydrogenation in the presence of water.

The process object of the present invention is further characterized by comprising the following operations:

a) Converting n-butane to MAN by catalytic vapour phase oxidation.

b) Recovering MAN from the effluent gases from the butane oxidation by selective absorption into GBL, forming a MAN-GBL mixture.

c) Removing water from the MAN-GBL mixture in a stripper, under the action of a gas and/or under vacuum, producing a MAN-GBL mixture with a minimum water and maleic acid content.

d) Recovering GEL from the exhaust gases that leave the maleic anhydride absorber, by water absorption;

e) Dehydrating the GBL recovered and recycling it to the maleic anhydride absorber;

f) Hydrogenating the dewatered MAN-GBL mixture over suitable catalyst(s) under conditions that favour THF and GBL formation.

g) Separating THF, GBL and by-products from the resulting hydrogenation mixture, by distillation.

h) Recycling a GBL rich stream to the MAN selective absorption.

The main advantages of the process object of the present invention can be summarized as follows:

a) It does not use an extraneous organic product as a solvent, such as dioxane, which would be difficult to recover and purify.

b) It avoids the use of a large excess of water as in the case of the processes wherein a maleic acid solution is used, and wherein high energy consumptions are required for water separation and THF and GBL recovery.

c) It avoids to feed corrosive maleic acid to the hydrogenation reactor, which would require expensive construction material, as for instance hastelloy.

d) A non refined fraction of the GEL product is used as solvent for the maleic anhydride absorption, allowing an optimum integration of the maleic anhydride process with the hydrogenation process.

e) THF and GBL are obtained from MAN in high yields.

Assuming that MAN is produced by a total recycle, high productivity process, wherein oxygen is used as the oxidizing medium, the process object of the present invention is able to produce GEL and THF with a consuption that approaches 1 Ton of butane per Ton of GBL equivalent, with reduced investment and optimized operating costs.

DESCRIPTION OF PREFERRED EMBODIMENTS

The sequence of the operations involved in the process object of the present invention is shown in FIG. 1.

The process of this invention is valid for any process wherein n-butane is converted to maleic anhydride by catalytic vapour phase oxidation.

The effluent gases from the maleic anhydride reactor (line 1) are conveyed to an absorber (2) where MAN is recovered by countercourrent washing with a GEL rich stream being recycled from the hydrogenation unit (line 3) and from a GBL stream recovered from the exhaust effluent gases (line 9).

In the lower section of the absorber (2), the resulting MAN-GBL mixture is contacted with a gas stream (line 4).

Under the gas and heat stripping action, most of the water countained in the MAN-GBL mixture is removed.

The outlet operating pressure at the absorber (2) ranges from 1.2 to 6.5 bar.

The operating temperature is controlled in such a way as to limit water condensation within the organic liquid effluent, being at least 10° C. above water's dewpoint.

The gases leaving the absorber (2) are conveyed (line 5) to the lower section of a scrubber column (6) where the GBL trapped by the exhaust gases is recovered by washing with water.

The aqueous GBL solution that leaves the water scrubber (6) is fed (line 7) to a dewatering column (8) which separates a GBL rich stream that flows back (line 9) to the absorber (2).

The overhead separation water from the dewatering column (8) is disposed of (line 10).

The excess water produced in the maleic anhydride converter (line 11) is removed in the upper section of the water scrubber (6).

The exhaust gases leaving the water scrubber (6) are recycled (line 12) to the the maleic anhydride plant reaction system.

The liquid effluent from the absorber(2), a MAN-GBL stream with a minimum water and maleic acid content, flows (line 13) to the hydrogenation unit.

Our concept of hydrogenation involves one or more, preferably two, catalytic stages.

In the hydrogenation unit, the DAN-GBL stream (line 13) is mixed with a preheated hydrogen stream (line 14) and both of them, after final preheating (15), flow (line 16) to the first hydrogenation stage (17).

The overall hydrogenation operating conditions and major performances are:

| | |
|---|---|
| Pressure: | from 20 to 80 bar, preferably from 30 to 50 bar |
| Temperature: | from 120° to 280° C., preferably from 170 to 240° C. |
| $H_2$ to MAN molar ratio: | from 20 to 150, preferably from 40 to 60 |
| $H_2$ space velocity: | from 500 to 4000 $hr^{-1}$ preferably from 2000 to 3000 $hr^{-1}$ |
| Conversion of MAN: | from 96% to 100% |
| Selectivity to GBL: | from 88% to 95% |
| Selectivity to THF: | from 1% to 10% |

Total selectivity to GBL+THF: from 90% to 98% When more than one stage of catalyst is employed, the catalyst of the first stage will hydrogenate maleic anhydride into succinic anhydride and will also carry out part of the hydrogenation of succinic anhydride to gamma butyrolactone.

A preferred catalyst of the first stage of hydrogenation is a catalyst comprising a noble metal of group VIII of the Periodic Table, preferably palladium or a compound thereof, on a support, preferably carbon or an inert oxide.

For the purposes of this description such a catalyst will be identified as Pd catalyst. The quantity of catalytically active substance in the Pd catalyst is from 0.1% to 10% by weight of the total weight of the catalyst, preferably from 0.2% to 2% by weight. Another preferred catalyst of the first stage of hydrogenation will be a nickel based catalyst, which may be used with or without a carrier. For the purposes of this description such a catalyst will be identified as Ni catalyst. The quantity of catalytically active substance in the supported Ni catalyst is from 1% to 50% by weight of the total weight of the catalyst, preferably from 5% to 2% by weight.

A preferred catalyst which can be used to perform the hydrogenation comprises an element of group VII B of the Mendeleef Periodic Table, preferably rhenium or a compound thereof, associated with at least one noble metal of group VIII of such Periodic Table, preferably palladium or a compound thereof, on a support, preferably carbon or an inert oxide. For the purposes of this description, such a catalyst may be identified as Pd-Re catalyst.

The Pd-Re catalyst can be used in hydrogenation in either one of the following configurations:

a) Hydrogenation reaction consisting of one stage only b) Hydrogenation reaction consisting of two or more stages c) Hydrogenation reaction consisting of two or more stages where the first stage uses a Pd catalyst or a Ni catalyst.

The quantity of catalytically active substance on the Pd-Re catalyst is from 0.1% to 10% by weight of the total weight of catalyst, preferably from 1% to 5% by weight.

The weight ratio of element of group VII B, preferably rhenium, to the noble metal of group VIII, preferably palladium, is from 1:1 to 10:1, preferably from 2:1 to 5:1.

Other preferred catalysts used either to perform the hydrogenation in place of the Pd-Re catalyst in either one of the configurations referred to above, are catalysts of the palladium-nickel type or catalysts of the palladium-copper type. For the purposes of this description catalysts of palladium-nickel type will be identified as Pd-Ni catalysts, and catalysts of palladium-copper type will be identified as Pd-Cu catalysts.

The quantity of catalytically active substance in the Pd-Ni or in the Pd-Cu catalysts is from 1% to 5% by weight of the total weight of the catalyst preferably from 5% to 20% by weight.

The weight ratio of either nickel or copper to palladium in said catalysts is from 0.5:1 to 50:1, preferably from 5:1 to 20:1.

Using a Pd catalyst in the first stage of hydrogenation to saturate maleic anhydride into succinic anhydride and to convert part of succinic anhydride into gamma butyrolactone is advantageous due to the inferior cost of Pd catalyst compared to Pd-Re, Pd-Ni or Pd-Cu catalysts.

After each stage a stream of cold hydrogen is injected to control the temperature of reaction.

This is shown in FIG. 1 as a stream of hydrogen (line 18) entering the reactor after the first stage (17), cooling the mixture entering the second stage (19).

As an alternative the effluent from each stage may be cooled by indirect heat exchange.

The effluent of reaction (line 20) will contain, besides GBL and THF, hydrogen, water, light organics (such as propanol, butanol, propionic acid, butyric acid), heavy organics (succinic acid, butanediol).

The effluent is cooled first by exchanging heat (21) with hydrogen and then in the cooler (22).

The cooled effluent (line 23) enters the separator (24), from which a hydrogen rich stream flows overheads (line 25).

A small fraction of the hydrogen is purged (line 26) to avoid accumulation of inerts. The remaning fraction flows to the compressor (27).

Fresh hydrogen (line 29) joins the compressed hydrogen rich gas (line 28).

A portion of the compressed hydrogen flows (line 18) to the interstages of the reactor to control the temperature of reaction. Another fraction (line 30) is preheated (21) and mixed with the feed to the hydrogenation reactor.

The liquid phase leaving the separator (24) flows (line 31) to a fractionation unit (32) which separates THF product (line 33), water and light organics (line 34), GEL product (line 35), heavy ends (line 36). A crude GEL rich stream, containing some heavy organics, is recycled (line 3) to the absorber (2) of the maleic anhydride plant.

According to this concept neither heavies nor lights can accumulate in the crude GEL used as absorption medium.

The only purge necessary is in the standard purification of the products.

The embodiments of the present invention are evidenced by Example A hereinafter.

EXAMPLE A

A typical composition (% by volume) of the gases exiting the maleic anhydride reactor (line 1), in a total recycle oxidation process, using oxygen as oxidizing medium, is as follows:

| | |
|---|---|
| Oxygen | 4.4% |
| Water steam | 11.1% |
| Butane | 3.6% |
| Carbon monoxide | 22.9% |
| Carbon dioxide | 56.6% |
| Maleic anhydride | 1.4% |
| Organic by products | traces |
| Inerts | traces |
| Flowrate: | 85042 Kg/hr |
| Pressure: | 3.5 Barg |

The effluent gases enter the absorber (2) where MAN is absorbed into a GBL rich stream (line 3), which is made up of 6352 Kg/hr recycled from the hydrogenation unit, plus a stream of dewatered GBL (line 9) recovered from the exhaust gases.

About 3000 Kg/hr of gas, preferably carbon dioxide, are fed (line 4) to the lower section of the absorber (2), in order to remove the major amount of water contained in the MAN—GEL mixture.

About 3100 Kg/hr of MAN are recovered, dissolved in the GBL rich stream.

The bottom product of the absorber (line 13) has the following typical composition (% by weight):

| | |
|---|---|
| MAN | 32.3% |
| GBL | 66.6% |
| Organic by products | 1.1% |

The water content in such stream will not exceed 1% by weight.

The effluent gases from the absorber (line 8) contain about 800 Kg/hr of entrained GBL and traces of MAN, which can be recovered by absorption in water in the lower section of the scrubber (6).

The recovered GBL (line 7) is dissolved in water, an average composition being 35% wt GBL, 65% wt water.

The aqueous GBL stream (line 7) flows to the dewatering column (8), which separates overheads water with traces of organics to be disposed of (line 10).

At the bottom of the dewatering column (8) is recovered a GBL rich stream containing residual water. In the upper section of the scrubber (6) is removed the excess of water produced in the maleic anhydride converter (line 11).

The exhaust gases leaving the water scrubber (line 12) are recycled to the maleic anhydride reaction system. The stream of recovered MAN in GBL (line 13), about 9700 Kg/hr, enters the hydrogenation section and, after mixing with hydrogen (line 14) and preheating (15), feeds the first stage of the hydrogenation reactor (17).

The reactor is of adiabatic type, a Pd on carbon catalyst being installed in the first stage of the reactor (17) and a Pd-Re on carbon catalyst in the following stage (19).

Quenching with cold hydrogen (line 18) is provided on the intestage to control the temperature.

The reaction conditions adopted in this example are:

| | |
|---|---|
| Pressure | 40 bar |
| Temperature | from 160° C. to 260° C. |
| Inlet H$_2$/MAN molar ratio | 40 |
| H$_2$ space velocity | 2000 hr$^{-1}$ |

In the above conditions the average performances of the reaction have been measured as follows:

| | |
|---|---|
| Conversion: | over 99% |
| Selectivity to GBL: | 93.4% |
| Selectivity to THF: | 4.8% |

The overall material balance of the hydrogenation results as follows:
Entering

| | |
|---|---|
| Organic feed | 9700 Kg/hr |
| Hydrogen | 140 Kg/hr |
| Total | 9840 Kg/hr |

| Products and by products | |
|---|---|
| GBL | 2520 Kg/hr |
| THF | 110 Kg/hr |
| GBL recycled to MAN absorber | 6352 Kg/hr |
| Water | 770 Kg/hr |
| By products | 78 Kg/hr |
| Hydrogen purge | 10 Kg/hr |
| Total | 9840 Kg/hr |

What is claimed is:
1. A process for production of gamma-butyrolactone and tetrahydrofuran by the hydrogenation of maleic anhydride recovered from a process of conversion of n-butane by catalytic vapor phase oxidation, comprising the following steps:
 a) Converting n-butane to maleic anhydride by catalytic vapor phase oxidation;
 b) Recovering maleic anhydride from effluent gases of a butane oxidation by selective absorption in a gamma butyrolactone rich stream, forming a maleic anhydride-gamma butyrolactone mixture;
 c) Removing water from said maleic anhydride-gamma butyrolactone mixture in a stripper under action of a gas producing a maleic anhydride-gamma butyrolactone mixture with minimum water and maleic acid content;
 d) Recovering gamma butyrolactone contained in exhaust gases leaving a maleic anhydride absorber, by absorption in water;
 e) Dehydrating said recovered gamma butyrolactone and recycling it to said maleic anhydride absorber;
 f) Hydrogenating said dewatered maleic anhydride-gamma butyrolactone mixture over a suitable catalyst (s), under conditions favouring the formation of gamma butyrolactone and tetrahydrofuran to form a hydrogenation mixture;
 g) Separating by distillation tetrahydrofuran, gamma butyrolactone and by products from said hydrogenation mixture and
 h) Recycling a gamma butyrolactone rich stream to select absorption of maleic anhydride.

2. The process according to claim 1, wherein the weight ratio between gamma butyrolactone and maleic anhydride in the mixture to be hydrogenated is from 3 to 1.

3. The process according to claim 1, wherein the absorption of maleic anhydride is from the effluent gases of a maleic anhydride converter which is operated at an outlet pressure from 1.2 to 6.5 bar and at an average operating temperature of 50 to 120° C.

4. The process according to claim 1, wherein the removal of water from the maleic anhydride-gamma butyrolactone mixture formed in the absorber is performed by a stripping action of carbon dioxide.

5. The process according to claim 1, wherein the removal of water from the maleic anhydride-gamma butyrolactone mixture formed in the absorber is performed by stripping the mixture under vacuum.

6. The process according to claim 1, wherein the recovery of gamma butyrolactone contained in the exhaust gases leaving the maleic anhydride absorber, is performed by absorption in and desorption from water.

7. The process according to claim 1, wherein the process of conversion of n-butane into maleic anhydride by catalytic vapor phase oxidation is either a once-through air based process, a partial recycle process using air or enriched air as oxidizing medium, or a total recycle process using oxygen as oxidizing medium.

8. The process according to claim 1, wherein a catalytic reactor for conversion of n-butane into maleic anhydride is either of the fixed, fluid, or transport bed type.

9. The process according to claim 1, further comprising feeding a mixture of hydrogen and maleic anhydride in a molar ratio of 20 to 70 in a hydrogenation reactor.

10. The process according to claim 1, wherein the hydrogenation is operated in one or more stages, on the same or on different catalysts, and wherein the catalyst of the first stage will hydrogenate maleic anhydride into succinic anhydride and will also carry out part of the hydrogenation of succinic anhydride to gamma butyrolactone.

11. The process according to claim 10, wherein the catalyst used in the first stage of hydrogenation will be a catalyst comprising palladium on a support comprising carbon or an inert oxide.

12. The process according to claim 11, wherein the quantity of palladium is from 0.2% to 2% of the total weight of the catalyst.

13. The process according to claim 10, wherein the catalyst used in the first stage of hydrogenation is a nickel based catalyst, with or without a support.

14. The process according to claim 13, wherein the quantity of catalytically active substance in said catalyst is from 5% to 20% by weight of the total weight of the catalyst.

15. The process according to claim 10, wherein the catalyst used to perform the hydrogenation either in one stage only or in two or more stages of hydrogenation comprises rhenium or a compound thereof, associated with palladium or a compound thereof on a support, said support comprising carbon or an inert oxide.

16. The process according to claim 15, wherein said catalyst is used only in the stage(s) following the first stage of hydrogenation.

17. The process according to claim 15, wherein the quantity of catalytically active substances in said catalyst is from 1% to 5% by weight of the total weight of the catalyst.

18. The process according to claim 15, wherein the weight ratio of rhenium to palladium is from 5 to 2.

19. The process according to claim 10, wherein the catalyst used to perform the hydrogenation either in one stage only or in two or more stages of hydrogenation is a catalyst comprising palladium and nickel.

20. The process according to claim 19, wherein said catalyst is used only in the stage(s) following the first stage of hydrogenation.

21. The process according to claim 16, wherein the quantity of catalytically active substance in said catalyst is from 5% to 20% by weight of the total weight of the catalyst.

22. The process according to claim 19, wherein the weight ratio of nickel to palladium is from 20 to 5.

23. The process according to claim 10, wherein the catalyst used to perform the hydrogenation either in one stage only or in two or more stages of hydrogenation is a catalyst comprising palladium and copper.

24. The process according to claim 23, wherein said catalyst is used only in the stage(s) following the first stage of hydrogenation.

25. The process according to claim 23, wherein the quantity of catalytically active substance in said catalyst is from 1% to 50% by weight of the total weight of the catalyst.

26. The process according to claim 23, wherein the weight ratio of copper to palladium is from 50 to 0.5.

27. The process according to claim 9, wherein the operating pressure at the first stage of hydrogenation is from 30 to 60 bar.

28. The process according to claim 9, wherein the operating temperature in the first stage of hydrogenation is from 160 to 220° C.

29. The process according to claim 9, wherein the operating pressure at the stage(s) following the first stage is from 30 to 60 bar.

30. The process according to claim 9, wherein the operating temperature in the stage(s) following the first stage is from 180° to 260° C.

31. The process according to claim 9, wherein the hydrogenation reactor is either of the isothermal or of the adiabatic type.

* * * * *